United States Patent
Dale et al.

(10) Patent No.: US 12,053,170 B2
(45) Date of Patent: Aug. 6, 2024

(54) MEDICAL DEVICE FOR CLOSURE OF A VASCULAR ABNORMALITY

(71) Applicant: St. Jude Medical, Cardiology Division, Inc., St. Paul, MN (US)

(72) Inventors: Theodore P. Dale, Corcoran, MN (US); Tracee Eidenschink, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 86 days.

(21) Appl. No.: 17/586,032

(22) Filed: Jan. 27, 2022

(65) Prior Publication Data

US 2022/0240912 A1 Aug. 4, 2022

Related U.S. Application Data

(60) Provisional application No. 63/143,064, filed on Jan. 29, 2021.

(51) Int. Cl.
*A61B 17/00* (2006.01)
*A61B 17/12* (2006.01)

(52) U.S. Cl.
CPC ...... *A61B 17/0057* (2013.01); *A61B 2017/00592* (2013.01); *A61B 2017/00623* (2013.01); *A61B 2017/00632* (2013.01); *A61B 2017/00867* (2013.01)

(58) Field of Classification Search
CPC .......... A61B 17/0057; A61B 17/12122; A61B 17/12172; A61B 2017/00592; A61B 2017/00623; A61B 2017/00632; A61B 2017/00867; A61F 2/0063; A61F 2/01; A61M 1/34

See application file for complete search history.

(56) References Cited

U.S. PATENT DOCUMENTS

| | | | |
|---|---|---|---|
| 2004/0133236 A1* | 7/2004 | Chanduszko | A61B 17/0057 606/213 |
| 2006/0069408 A1* | 3/2006 | Kato | A61B 17/0057 606/213 |
| 2007/0270905 A1* | 11/2007 | Osborne | A61B 17/0057 606/213 |

(Continued)

OTHER PUBLICATIONS

European Search Report for related EP Patent Application No. 22153554.5, mailed Jul. 11, 2022, 10 pages.

*Primary Examiner* — Katherine M Rodjom
*Assistant Examiner* — Lindsey R. Rivers
(74) *Attorney, Agent, or Firm* — Armstrong Teasdale LLP (57) ABSTRACT

Described herein is a medical device including a medical device including a device body and a plurality of extensions. The device body includes a first side, a second side, and a plurality of expandable cells. The plurality of expandable cells have a proximal edge and a distal edge. The plurality of expandable cells extends laterally between and connects the first and second sides. The plurality of extensions extend longitudinally from each of the first and second sides. A first plurality of extensions extend proximally from a proximal end of each side to beyond the proximal edge and a second plurality of extensions extend distally from a distal end of each side to beyond the distal edge. The first and second pluralities of extensions have coiled ends.

20 Claims, 10 Drawing Sheets

(56) References Cited

U.S. PATENT DOCUMENTS

| | | | |
|---|---|---|---|
| 2008/0243151 A1* | 10/2008 | Binmoeller | A61B 1/041 |
| | | | 606/153 |
| 2008/0262518 A1 | 10/2008 | Freudenthal | |
| 2009/0228021 A1* | 9/2009 | Leung | A61B 17/06166 |
| | | | 606/151 |
| 2018/0333150 A1 | 11/2018 | Bak-Boychuk et al. | |
| 2020/0237507 A1* | 7/2020 | Noe | A61M 39/22 |

* cited by examiner

MEDICAL DEVICE FOR CLOSURE OF A VASCULAR ABNORMALITY

CROSS-REFERENCE TO RELATED APPLICATIONS

This application claims the benefit of priority to U.S. Prov. Pat. App. No. 63/143,064 filed Jan. 29, 2021, which is incorporated by reference herein in its entirety.

BACKGROUND OF THE DISCLOSURE

A. Field of Disclosure

The present disclosure relates generally to medical devices that are used in the human body. In particular, the present disclosure is directed to a medical device for closure of a vascular abnormality by securing two pieces of vascular tissue together.

B. Background

Medical devices are used to treat a variety of different target sites in the body, including abnormalities, vessels, organs, openings, chambers, channels, holes, cavities, and the like. At least some medical devices are formed from shape-memory material in a braided web configuration. At least some of these devices are permanently implanted within a patient's body at a target site to achieve an occlusive function.

Percutaneous procedures are becoming more prevalent in surgical procedures. At least some percutaneous procedures access the left atrium through the septal wall. Additionally, many patients (e.g., approximately 10-20% of the population) have a patent foramen *ovale* (PFO), which can be closed at any age. Conventional devices for closing PFOs include, for example, a braided-web closure device that is implanted in the septal wall. To cross the septal wall in a patient with a previously-closed PFO (e.g., to treat atrial fibrillation) a physician may need to navigate through the braided-web closure device.

SUMMARY OF THE DISCLOSURE

The present disclosure is directed to a medical device including a device body and a plurality of extensions. The device body includes a first side, a second side, and a plurality of expandable cells. The plurality of expandable cells have a proximal edge and a distal edge. The plurality of expandable cells extends laterally between and connects the first and second sides. The plurality of extensions extend longitudinally from each of the first and second sides. A first plurality of extensions extend proximally from a proximal end of each side to beyond the proximal edge and a second plurality of extensions extend distally from a distal end of each side to beyond the distal edge. The first and second pluralities of extensions have coiled ends.

The present disclosure is further directed to a delivery system for delivering a medical device to a target site. The delivery system includes a medical device and a delivery device coupled to the medical device. The medical device includes a device body and a plurality of extensions. The device body includes a first side, a second side, and a plurality of expandable cells. The plurality of expandable cells have a proximal edge and a distal edge. The plurality of expandable cells extends laterally between and connects the first and second sides. The plurality of extensions extend longitudinally from each of the first and second sides. A first plurality of extensions extend proximally from a proximal end of each side to beyond the proximal edge and a second plurality of extensions extend distally from a distal end of each side to beyond the distal edge. The first and second pluralities of extensions have coiled ends. The delivery device includes a catheter and a delivery cable. The medical device is coupled to the delivery cable, and the delivery cable is configured to be advanced through the catheter to deploy the medical device at the target site.

The present disclosure is further directed to a method for closing a Patent Foramen *Ovale* (PFO). The method includes providing a medical device, advancing the medical device to the PFO using a delivery system including a catheter and a delivery cable, positioning the medical device relative to the PFO to secure a septum *primum* and septum *secundum* together, and de-coupling the medical device from the delivery cable to deploy the medical device. The medical device includes a device body and a plurality of extensions. The device body includes a first side, a second side, and a plurality of expandable cells. The plurality of expandable cells have a proximal edge and a distal edge. The plurality of expandable cells extends laterally between and connects the first and second sides. The plurality of extensions extend longitudinally from each of the first and second sides. A first plurality of extensions extend proximally from a proximal end of each side to beyond the proximal edge and a second plurality of extensions extend distally from a distal end of each side to beyond the distal edge. The first and second pluralities of extensions have coiled ends.

BRIEF DESCRIPTION OF THE DRAWINGS

Corresponding reference characters indicate corresponding parts throughout the several views of the drawings. It is understood that Figures are not necessarily to scale.

DETAILED DESCRIPTION OF THE DISCLOSURE

The present disclosure relates generally to medical devices that are used in the human body. In particular, the present disclosure is directed to a medical device embodied as a clip configured to secure two pieces of tissue together. More specifically, the present disclosure is directed to a clip device that closes a patent foramen *ovale* (PFO) to facilitate proper blood flow within the heart while reducing an amount of material (e.g., providing a device without braided-web discs) providing such closure. Accordingly, the medical devices of the present disclosure may enable an improvement in crossing the septal wall during future medical procedures while maintaining efficacy in closing the PFO.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

Although the exemplary embodiment of the medical device is described as treating a target site including a PFO, it is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as a left atrial appendage (LAA), an atrial septal defect, a lesion, a vessel dissection, or a tumor. Embodiments of the medical device may be useful, for example, for occluding an atrial septal defect (ASD), a ventricular septal defect (VSD), or a patent ductus arteriosus (PDA). Furthermore, the term "lumen" is also not meant to be limiting, as the vascular abnormality may reside in a variety of locations within the vasculature, such as a vessel, an artery, a vein, a passageway, an organ, a cavity, or the like. As used herein, the term "proximal" refers to a part of the medical device or the delivery device that is closest to the operator, and the term "distal" refers to a part of the medical device or the delivery device that is farther from the operator at any given time as the medical device is being advanced through the delivery device.

The medical device may include a device body including a first side, a second side, and a plurality of expandable cells. The plurality of expandable cells have a proximal edge and a distal edge. The plurality of expandable cells extends laterally between and connects the first and second sides. The medical device also includes a plurality of extensions extending longitudinally from each of the first and second sides. A first plurality of extensions extend proximally from a proximal end of each side to beyond the proximal edge and a second plurality of extensions extend distally from a distal end of each side to beyond the distal edge. The first and second pluralities of extensions have coiled ends.

The present disclosure will now be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

Figure 1:
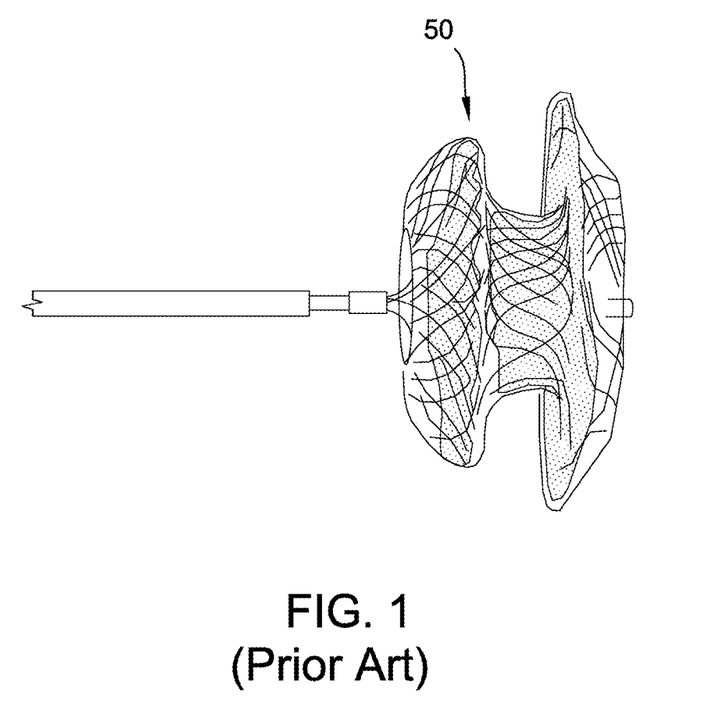
FIG. 1 illustrates a known medical device utilized for occlusion.

At least some conventional or known medical devices, such as a medical device 50 shown in FIG. 1, are formed from shape-memory material in a braided configuration. These devices utilize a braided mesh configuration to facilitate thrombosis by tensioning the tissue of the defect to seal a vascular abnormality. The collection of the endothelialization cells in the mesh allows for the device to provide an occlusive effect. However, if the patient later requires a medical procedure that involves crossing over or through the implanted device, the physician must navigate through the braided material and the ingrowth. This may increase the duration of a procedure and/or may adversely impact the sealing function of the medical device 50, which may require an additional or extended procedure to implant a new medical device.

The medical devices of the present disclosure enable the closure of an abnormality while reducing the amount of material implanted in the body, compared to known devices. The devices of the present disclosure utilize a cellular frame configuration for the device body of the medical device (e.g., a plurality of expandable cells) to facilitate tissue proximity or closure by tensioning the defect to stretch down on itself to seal a vascular abnormality. Accordingly, the medical device of the present disclosure reduces or eliminates the above-described disadvantages of known medical devices while providing a sufficient closure and sealing effect.

Figure 2:
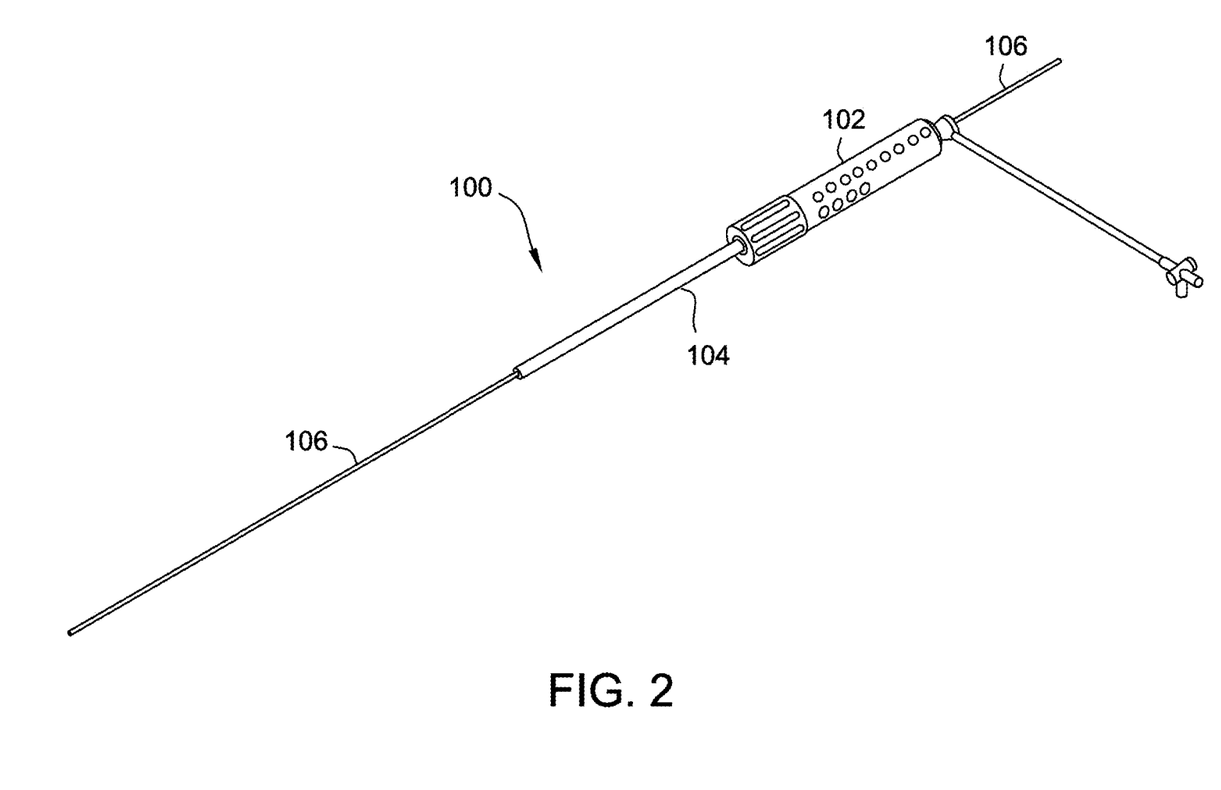
FIG. 2 is a schematic view of an exemplary embodiment of a delivery system for deploying a medical device.

Turning now to FIG. 2, a schematic diagram of a delivery system 100 is shown. Delivery system 100 includes a delivery device 102 that includes a catheter 104 and a delivery cable 106 for deployment of a medical device 108 (see FIG. 3A) at a target site.

Figures 3A, 3B:
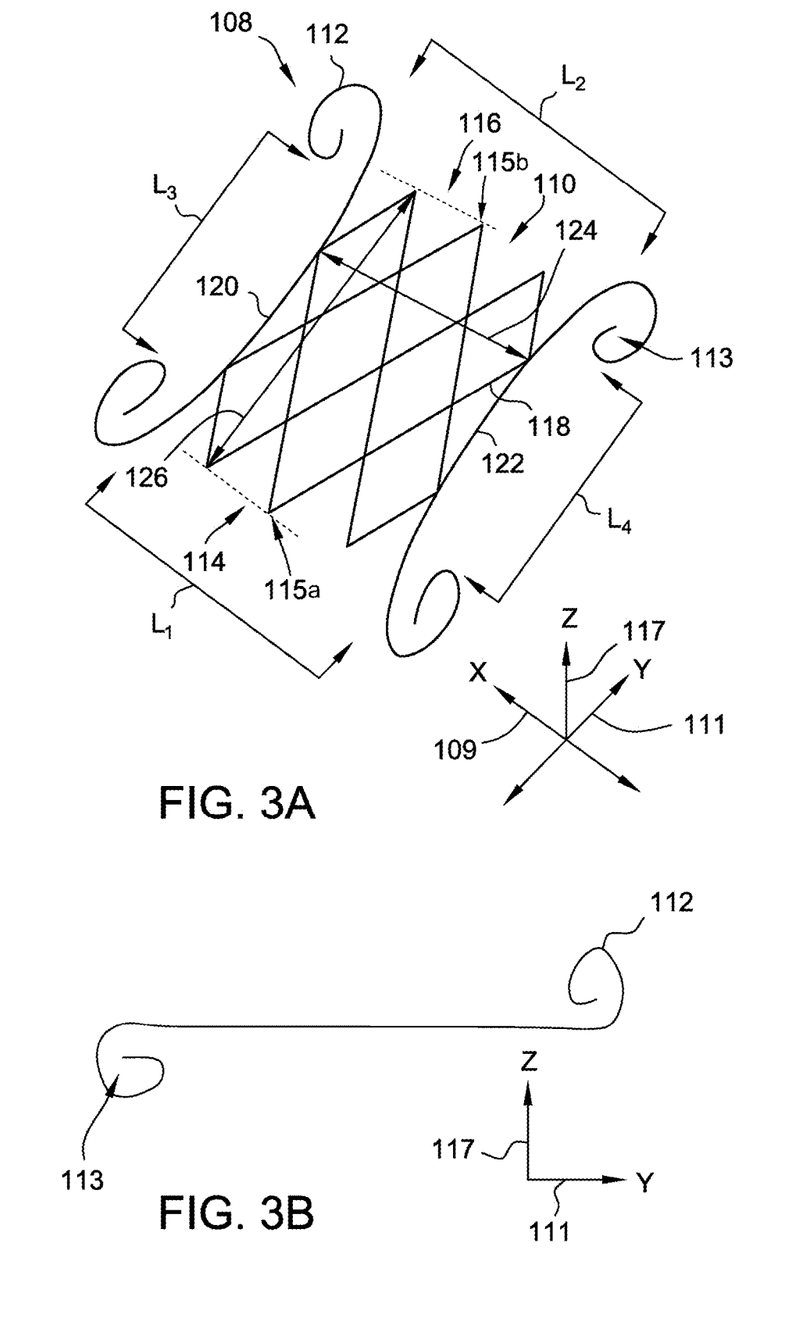
FIGS. 3A and 3B depict an exemplary embodiment of a medical device in accordance with the present disclosure.

FIGS. 3A-9 depict various exemplary embodiments of a medical device 108 in accordance with the present disclosure. Broadly, medical device 108 includes a device body 110 and a plurality of extensions 112 extending from device body 110. With reference first to FIGS. 3A and 4A, device body 110 includes a first side 120, a second side 122, and a plurality of expandable cells 118 having a proximal edge 114 (dotted line 114 shown in FIGS. 3A and 4A) defined at least in part by proximal-most peripheral points 115a of cells 118, and a distal edge 116 (dotted line 116 shown in FIGS. 3A and 4A) defined at least in part by distal-most peripheral points 115b of cells 118. First side 120 and second side 122 are coupled to the plurality of expandable cells 118 such that the plurality of expandable cells 118 extend laterally between and connect first side 120 and second side 122. Each side 120, 122 adjoins proximal edge 114 and distal edge 116, such that device body 110 is bounded by proximal edge 114, first side 120, distal edge 116, and second side 122. In some embodiments, a length of each side 120, 122 may be approximately equal to a longitudinal distance between proximal edge 114 and distal edge 116 (as measured in a Y-direction 111). In other embodiments, a length of each side 120, 122 may be greater than or less than a longitudinal distance between proximal edge 114 and distal edge 116.

Proximal edge 114 has a first length $L_1$, and distal edge 116 has a second length $L_2$. First length $L_1$ is approximately equal to second length $L_2$. A width of device body 110, measured in an X-direction 109, corresponds to first length $L_1$ and/or second length $L_2$. First side 120 has a third length $L_3$, and second side 122 has a fourth length $L_4$. Third length $L_3$ is approximately equal to fourth length $L_4$. A height or overall length of device body 110, measured in Y-direction 111, corresponds to third length $L_3$ and fourth length $L_4$. It is contemplated that first and second lengths $L_1$, $L_2$ may be approximately equal to third and fourth lengths $L_3$, $L_4$. It is also contemplated that first and second lengths $L_1$, $L_2$ may be greater than or less than third and fourth lengths $L_3$, $L_4$.

Extensions 112 extend longitudinally (in a Y-direction) from device body 110, i.e., extensions 112 extend proximally from device body 110 beyond proximal edge 114 and extend distally from device body 110 beyond distal edge 116. More specifically, extensions 112 extend in both proximal and distal directions from first and second sides 120, 122 and/or from between the plurality of expandable cells 118 of device body 110. In the exemplary embodiment of FIG. 3A, extensions 112 extend longitudinally from the first and second sides 120, 122 and may be integrally formed as proximal and distal ends of first and second sides 120, 122. Alternatively, extensions 112 may be suitably attached or coupled to first and second sides 120, 122 such that extensions 112 extend longitudinally from first and second sides 120, 122 in both proximal and distal directions. In other embodiments, one or more extensions 112 may additionally or alternatively extend longitudinally from the plurality of expandable cells 118, e.g., from between one or more cells 118 as well as from first and second sides 120, 122 (see FIG. 4A).

Extensions 112 are helical or coiled at free ends 113 thereof. The coiled ends 113 may coil anteriorly or posteriorly. That is, the ends 113 of extensions 112 may coil in a Z-direction 117, as shown more clearly in FIGS. 3B and 4B. It is also contemplated that the end 113 of one or more extensions 112 may coil anteriorly and the end 113 of one or more other extensions 112 may coil posteriorly. Alternatively, the ends 113 may coil substantially within the X-Y plane. The embodiments depicted in FIGS. 3-9 are contemplated to exemplify each of the coil configurations described above, depending on the embodiment. "Coiled," as used herein, refers generally to any particular helical, spiral, or coiled shape, such as any number of revolutions or partial revolutions of ends 113.

Figure 4A:
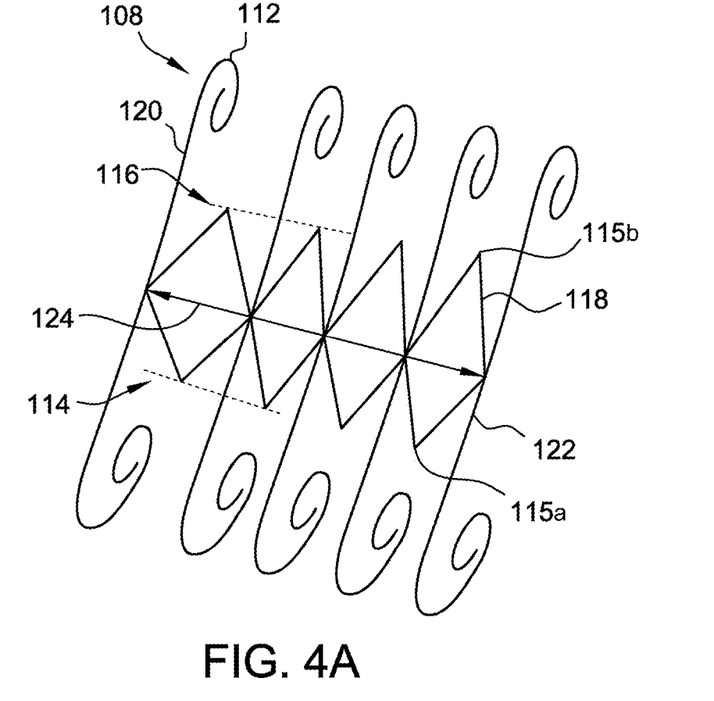
FIGS. 4A and 4B depict another embodiment of a medical device in accordance with the present disclosure.
Figure 4B:
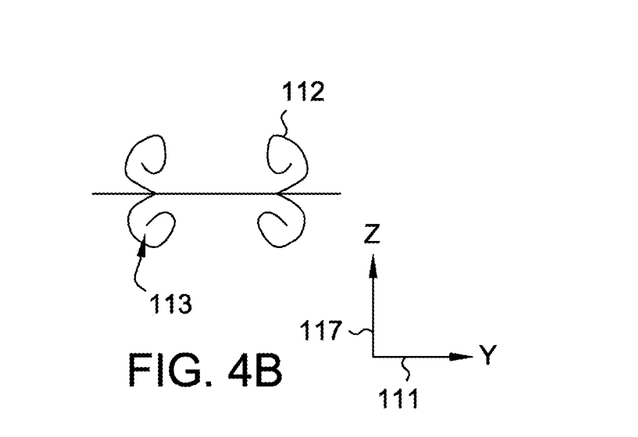
Figure 5:
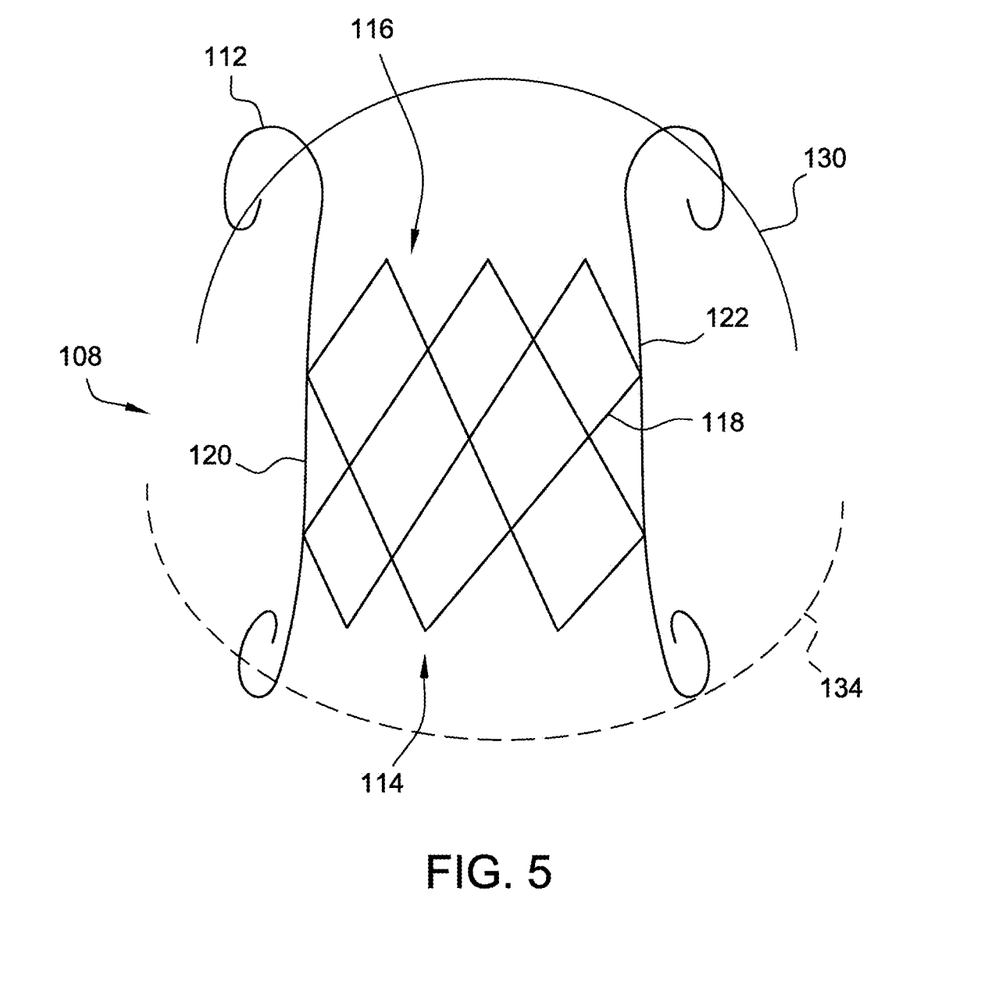
FIG. 5 depicts the medical device shown in FIG. 3 deployed at a target site.
Figure 6A:
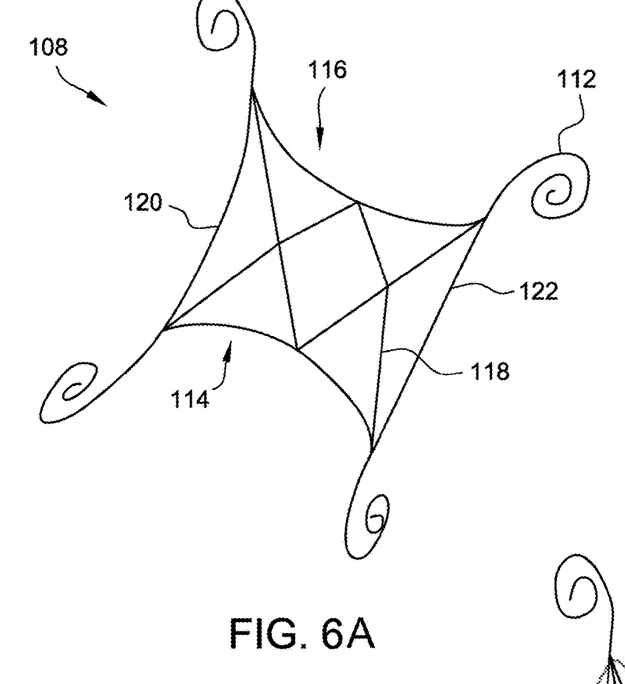
FIGS. 6A and 6B depict another embodiment of a medical device deployed at a target site.
Figure 6B:
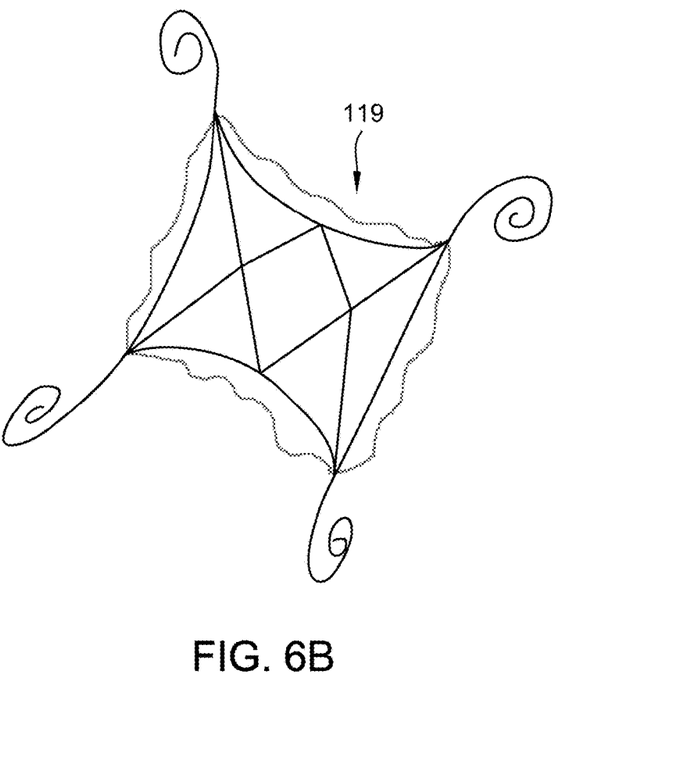
Figure 7:
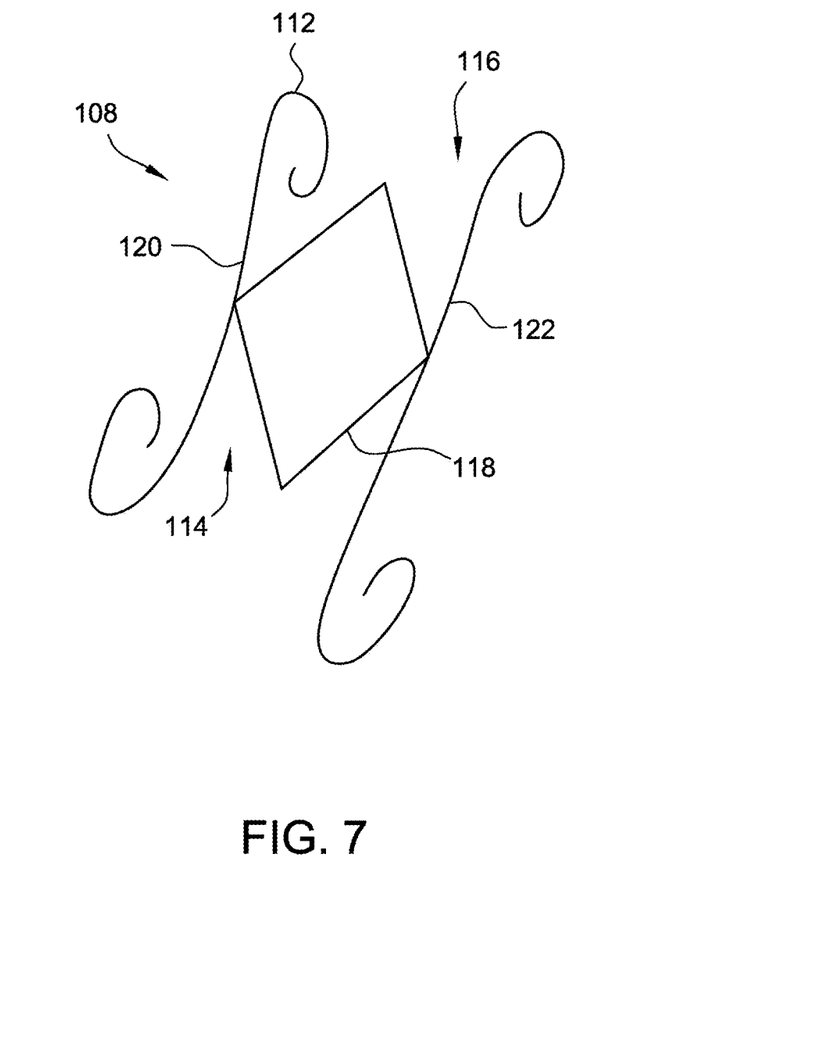
FIG. 7 depicts another embodiment of a medical device deployed at a target site.

In the exemplary embodiment, cells 118 are arranged in an array including a plurality of rows 124 (i.e., cells 118 extending laterally between first and second sides 120, 122) and a plurality of columns 126 (i.e., cells 118 extending longitudinally between proximal and distal edges 114, 116; see FIGS. 3A, 5, 6A & 6B). In another embodiment, cells 118 are arranged in an array including only a single row 124 of cells 118 extending between first and second sides 120, 122 (FIGS. 4A & 7). In another embodiment, cells 118 are arranged in an array including only a single column 126 of cells extending longitudinally between proximal and distal edges 114, 116 (see FIG. 7). Proximal and distal edges 114, 116 are defined at least in part by respective peripheral edges 115a, 115b of the array of cells 118. It is contemplated that the number of rows 124 and columns 126 of cells 118 in medical device 108 can be varied to give device body 110 different sizes and/or to adjust the amount of lateral stretch provided to achieve occlusive function at the target site.

In the illustrated embodiments, cells 118 are diamond shaped. It is contemplated that cells 118 can be of any shape and various sizes that allow for medical device 108 to achieve occlusion, including, without limitation, circular or ovular cells, or cells with irregular shapes. It is further contemplated that each of the embodiments of FIGS. 3-9 may have at least device body 110 encased in a fabric or polymer material 119 (as shown, for example, in FIG. 6B) for additional occluding effect. That is, depending on the embodiment, the plurality of expandible cells 118 may or may not be covered with a suitable fabric or polymer material 119 for additional sealing. Examples of suitable fabric or polymer material 119 include PET, urethane, Thorolon, HDMWPE, a bioabsorable fabric, and any other suitable fabric or polymer known by those of ordinary skill to provide an occlusive effect at the target site.

In the exemplary embodiment, medical device 108 is formed from an at least partially elastic material such that device body 110 is flat (e.g., having two dimensions (length and width) and occupying the X-Y plane). As described further herein, medical device 108 is delivered to a target site (e.g., a PFO) in a laterally constricted or compressed orientation (e.g., with a reduced width). When medical device 108 is deployed, medical device 108 is configured to expand to an original width, due to the elastic material. As described herein above, extensions 112 may extend out of the X-Y plane of the device body upon deployment depending on the embodiment. As described further herein, extensions 112 engage with adjacent opposing portions of tissue, such that the lateral spring force exerted by medical device 108, during deployment thereof, urges the opposing portions of tissue together in a direction normal to a plane defined by device body 110 (e.g., in Z-direction 117, see FIG. 8). In some embodiments, medical device 108 in its entirety is formed from one or more wires of a thin wire material such as single strand wire, multistrand wire, braided wire, wound wire ribbon, etc. In embodiments comprising wound wire ribbon, a flat and wide, yet thin, wire material is formed. In other embodiments, medical device 108 in its entirety may be formed from a laser-cut material. In some embodiments, device body 110 and extensions 112 are at least partially integrally formed. For example, one or more extensions 112 may be formed from a same wire as one or more cells 118 from which extensions 112 extend. In additional embodiments, device body 110 is formed from a laser-cut material and plurality of extensions 112 are formed from thin wire material (e.g., a single strand wire, a multistrand wire, or a braided wire) and coupled to device body 110 using any suitable attachment method. In certain embodiments, device body 110 is formed from a braided mesh material. In some such embodiments, ends 113 are implemented as unbraided ends of the material used to form the mesh; in other embodiments, ends 113 may be implemented as addition wires coupled to the braided mesh. It is contemplated that medical device 108 may be embodied as a two-dimensional device or a three-dimensional device.

In some embodiments, medical device 108 includes one or more attachment features 138 (see FIG. 9) coupled to one end of device body 110. Attachment features 138 enable coupling delivery cable 106 to medical device 108, for deployment of medical device 108 at the target site. Attachment features 138 may be implemented as tethers (e.g., that can be snared by a distal end of delivery cable) or as any other suitable attachment feature.

In one embodiment, medical device 108—specifically, device body 110 and/or extensions 112—is formed from a shape-memory material. One particular shape memory material that may be used is Nitinol. Nitinol alloys are highly elastic and are said to be "super-elastic," or "pseudo-elastic." This elasticity may allow medical device 108 to be resilient and return to a preset, expanded configuration for deployment following passage in a distorted form through delivery catheter 104. Further examples of materials and manufacturing methods for medical devices with shape memory properties, including braided mesh material, are provided in U.S. Pat. No. 8,777,974, titled "Multi-layer Braided Structures for Occluding Vascular Defects" and filed on Jun. 21, 2007, which is incorporated by reference herein in its entirety.

It is also understood that medical device 108 may be formed from various materials other than Nitinol that have elastic properties, such as stainless steel, trade named alloys such as Elgiloy®, or Hastalloy, Phynox®, MP34N (an alloy of nitinol, cobalt, chromium, and molybdenum), CoCrMo alloys, metal, polymers, or a mixture of metal(s) and polymer(s). Suitable polymers may include PET (Dacron™), polyester, polypropylene, polyethylene, HDPE, polyurethane, silicone, PTFE, polyolefins and ePTFE. In still other embodiments, medical device 108 is formed from a bioabsorbable material, which may be elastic or non-elastic.

In operation, medical device 108 is advanced towards the target site within catheter 104 of delivery device 102. Delivery device 102 is configured to engage with the septum *secundum* and/or the septum *primum* (e.g., to be advanced between the septum *secundum* and the septum *primum*, within the PFO tunnel). Further, in some embodiments, delivery device 102 can be configured to allow manipulation (e.g., deflection) of either the septum *secundum* or the septum *primum*, for example, to facilitate positioning medical device 108 relative to the septum *secundum* and/or the septum *primum*. Catheter 104 of the delivery system 100 may have any suitable size that enables medical device 108 and delivery system 100 to function as described herein. In some embodiments, the outer diameter of catheter 104 is in a range of about 4F to about 9F, depending on the size of the defect at the target site and, therefore, the size of the medical device to be deployed.

Once catheter 104 is advanced to the target site, medical device 108 is deployed from catheter 104 using delivery cable 106. In some embodiments, medical device 108 is deployed into an abnormality to be occluded. Delivery cable 106 facilitates positioning and/or orienting medical device 108 into a desired position at the target site. In one particular embodiment, for example, where medical device 108 is used to occlude a PFO, a first plurality of extensions 112 (e.g., a plurality of distal extensions 128, see FIG. 8) are positioned into engagement with the tissue of the septum *primum*, and a second plurality of extensions 112 (e.g., a plurality of proximal extensions 132, also shown in FIG. 8) are positioned into engagement with the tissue of the septum *secundum*. Extensions 112 engage with the respective tissue, as described herein, by ends 113 being embedded into the respective tissue. Additionally or alternatively, one or more portions of the coiled ends 113 of extensions 112 may engage against an outer surface of (and not enter into) the tissue.

Figure 8:
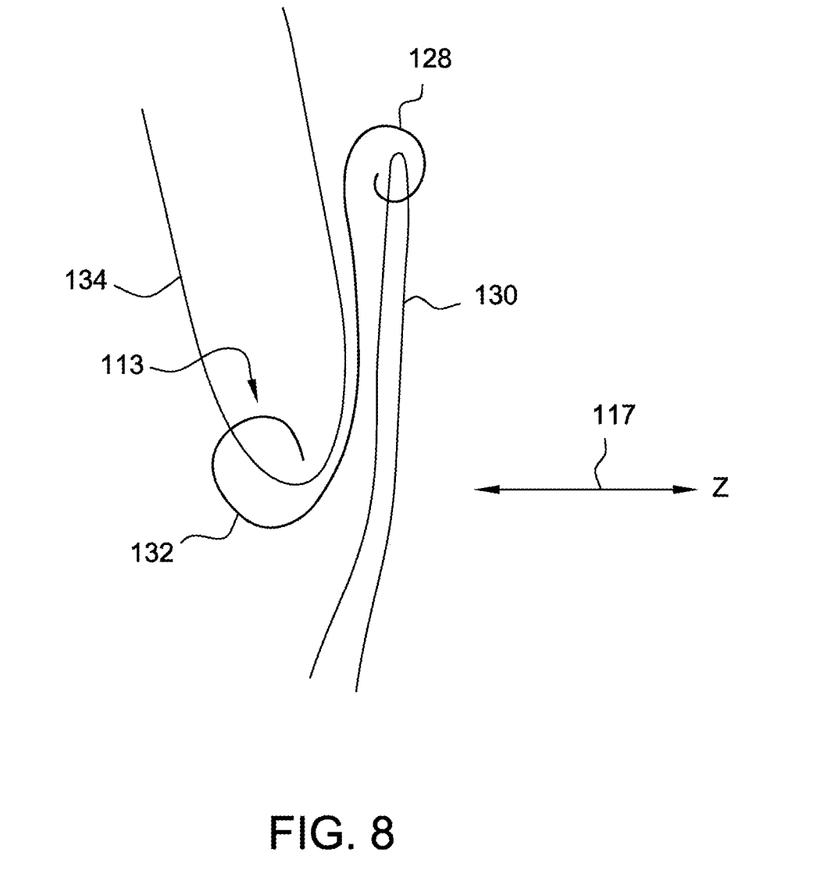
FIG. 8 is a side view of a medical device, in accordance with the present disclosure, deployed at a target site.
Figure 9:
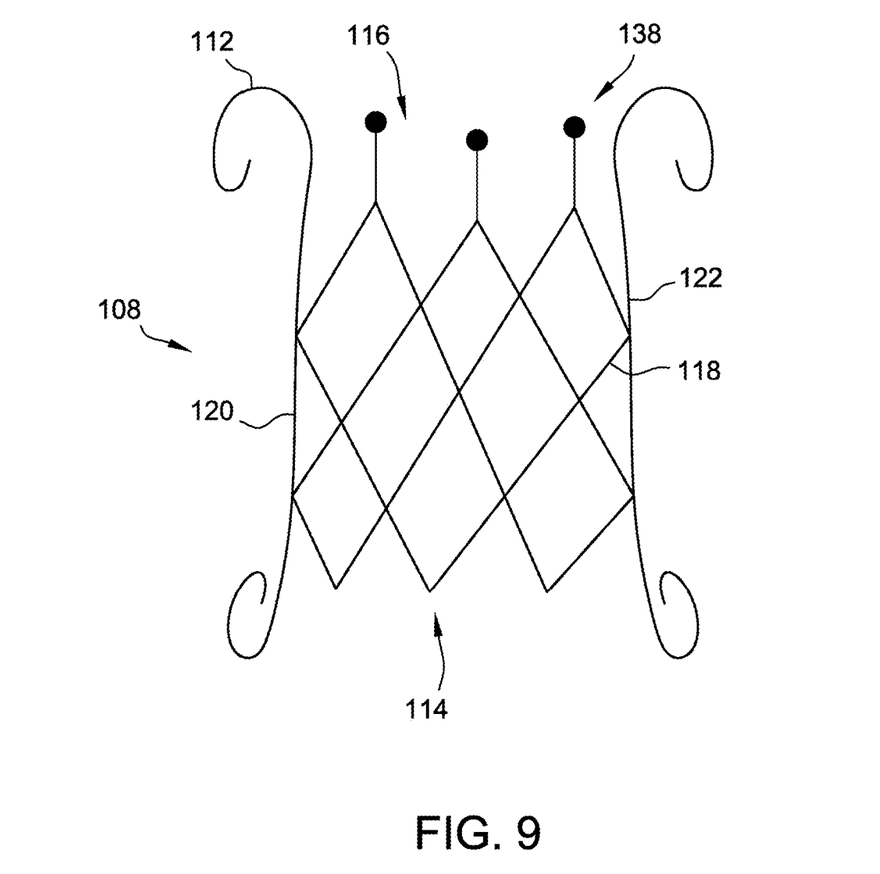
FIG. 9 depicts another embodiment of a medical device deployed at a target site and including an integrated attachment feature for delivery thereof.

Specifically, FIG. 8 illustrates a side view of medical device 108 in a deployed state, with ends 113 embedded into the tissue of a PFO. As shown in FIG. 8, distal extensions 128 engage the septum *primum* 130, and proximal extensions 132 engage the septum *secundum* 134, which opposes the septum *primum* 130 across the PFO tunnel. Medical device 108 is urged from its constricted delivery state back to its full width. Because extensions 112 (including distal extensions 128 and proximal extensions 132) are engaged with the tissue of the PFO, as medical device 108 laterally expands, septum *primum* 130 and septum *secundum* 134 are also each urged laterally, and thereby are contracted and held together in the Z-direction 117. The width of medical device 108 between first side 120 and second side 122 may be selected based on a size of the PFO to be sufficient to hold the septum *primum* 130 taut during the cardiac cycle. In addition, first length $L_1$ and second length $L_2$ may also be selected based on the size of the opening to be occluded.

The placement and positioning of medical device 108 may be assessed and confirmed (e.g., by a physician) prior to disconnecting delivery cable 106 of delivery device 102 from medical device 108.

Figure 10:
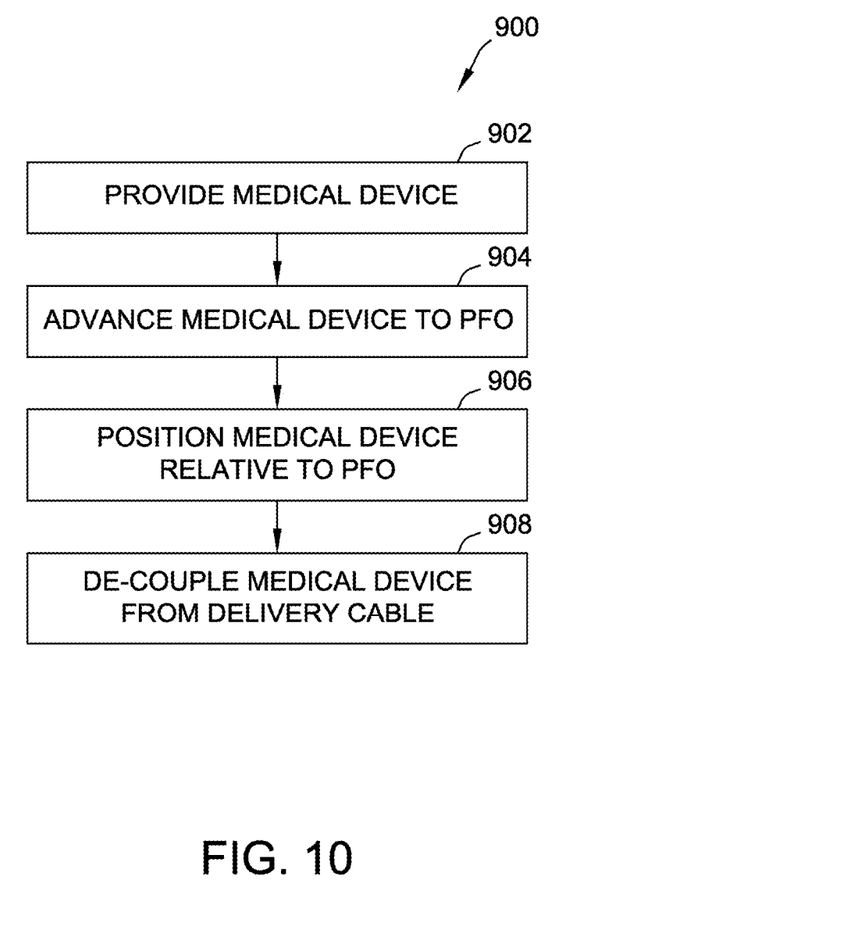
FIG. 10 is a flow diagram of an exemplary method of using a medical device to close a patent foramen *ovale* (PFO).

FIG. 10 is a flow diagram of an exemplary method 900 of using medical device 108 to close a PFO in a patient. In the exemplary embodiment, method 900 includes providing 902 a medical device. As described herein, the medical device includes a device body comprising a first side, a second side, and a plurality of expandable cells. The plurality of expandable cells have a proximal edge and a distal edge. The plurality of expandable cells extends laterally between and connects the first and second sides. The plurality of extensions extend longitudinally from each of the first and second sides. A first plurality of extensions extend proximally from a proximal end of each side to beyond the proximal edge and a second plurality of extensions extend distally from a distal end of each side to beyond the distal edge. The first and second pluralities of extensions have coiled ends.

Method 900 also includes advancing 904 the medical device to the PFO using a delivery system including a catheter and a delivery cable, positioning 906 the medical device relative to the PFO to secure a septum *primum* and septum *secundum* together, and decoupling 908 the medical device from the delivery cable to deploy the medical device.

Method 900 may include additional, alternative, and/or fewer steps, including those described herein. For example, in some embodiments, positioning 906 the medical device relative to the PFO includes advancing the medical device towards the PFO to deploy the distal end from the delivery catheter, wherein during deployment of the distal end, the coiled ends of the distal extensions engage the septum *primum* tissue. The delivery catheter is then retracted to deploy the proximal end from the delivery catheter, wherein during the deployment of the proximal end, the coiled ends of the proximal extensions engage the septum *secundum* tissue.

While embodiments of the present disclosure have been described, it should be understood that various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device comprising: a device body comprising a first side, a second side, and a plurality of expandable cells having a proximal edge and a distal edge, wherein the plurality of expandable cells extends laterally between and connects the first and second sides, the device body being planar and having a longitudinal axis; and a plurality of extensions extending longitudinally from each of the first and second sides, wherein a first plurality of extensions extend proximally from a proximal end of each side to free coiled ends located beyond the proximal edge, wherein each of the first plurality of extensions are separated by a distance at the proximal end of each side; and a second plurality of extensions extend distally from a distal end of each side to free coiled ends located beyond the distal edge, wherein each of the second plurality of extensions are separated by a distance at the distal end of each side.

2. The medical device of claim 1, wherein the plurality of expandable cells are arranged in an array including one or more rows and one or more columns.

3. The medical device of claim 1, wherein at least a portion of the coiled ends of the plurality of extensions coil anteriorly.

4. The medical device of claim 1, wherein at least a portion of the coiled ends of the plurality of extensions coil posteriorly.

5. The medical device of claim 1, wherein at least a first coiled end of the coiled ends of the plurality of extensions coils anteriorly and at least a second coiled end of the coiled ends of the plurality of extensions coils posteriorly.

6. The medical device of claim 1, wherein the device body is encased in a fabric or polymer material.

7. The medical device of claim 1, wherein the plurality of extensions additionally extend from between one or more of the plurality of expandable cells in both proximal and distal directions.

8. The medical device of claim 1, wherein the medical device is configured to be deployed to close a patent foramen ovale (PFO), and, when the medical device is deployed, the first plurality of extensions are configured to engage a surface of a septum secundum and the second plurality of extensions are configured to engage a surface of a septum primum to hold the septum secundum and the septum primum together during a cardiac cycle.

9. The medical device of claim 8, wherein a width of the medical device is selected based on a size of the PFO.

10. The medical device of claim 1, wherein the medical device comprises one of nitinol, stainless steel, an alloy of nitinol, cobalt, chromium, and molybdenum.

11. The medical device of claim 1, wherein the medical device is formed from at least one of a laser-cut material and a wire material.

12. The medical device of claim 11, wherein the device body is formed from the laser-cut material and the plurality of extensions are formed from the wire material.

13. A delivery system for delivering a medical device to a target site, the delivery system comprising:
a medical device comprising: a device body comprising a first side, a second side, and a plurality of expandable cells having a proximal edge and a distal edge, wherein the plurality of expandable cells extends laterally between and connects the first and second sides, the device body being planar and having a longitudinal axis; and a plurality of extensions extending longitudinally from each of the first and second sides, wherein a first plurality of extensions extend proximally from a proximal end of each side to free coiled ends, wherein each of the first plurality of extensions are separated by a distance at the proximal end of each side; and a second plurality of extensions extend distally from a distal end of each side to free coiled ends, wherein each of the second plurality of extensions are separated by a distance at the distal end of each side.

14. The delivery system of claim 13, wherein the target site is a patent foramen ovale (PFO), and wherein, when deployed, the medical device is configured to close the PFO.

15. The delivery system of claim 13, wherein the medical device is configured to secure a septum primum and a septum secundum together.

16. A method for closing a patent foramen ovale (PFO), the method comprising:
providing a medical device comprising: a device body comprising a first side, a second side, and a plurality of expandable cells having a proximal edge and a distal edge, wherein the plurality of expandable cells extends laterally between and connects the first and second sides, the device body being planar and having a longitudinal axis; and a plurality of extensions extending longitudinally from each of the first and second sides, wherein a first plurality of extensions extend proximally from a proximal end of each side to free coiled ends, wherein each of the first plurality of extensions are separated by a distance at the proximal end of each side; and a second plurality of extensions extend distally from a distal end of each side to free coiled ends, wherein each of the second plurality of extensions are separated by a distance at the distal end of each side;
advancing the medical device to the PFO using a delivery device including a delivery catheter and a delivery cable, wherein the medical device is coupled to the delivery cable;
positioning the medical device relative to the PFO to secure a septum primum and septum secundum together; and
de-coupling the medical device from the delivery cable to deploy the medical device.

17. The method of claim 16, wherein positioning the medical device comprises deploying a distal end of the medical device from the delivery catheter.

18. The method of claim 17, wherein the coiled ends of the second plurality of extensions engage with a tissue of the septum primum.

19. The method of claim 18, wherein positioning the medical device comprises retracting the delivery catheter to deploy a proximal end of the medical device from the delivery catheter.

20. The method of claim 19, wherein the coiled ends of the first plurality of extensions engage with a tissue of the septum secundum.

* * * * *